United States Patent
Kawabata

(10) Patent No.: US 10,832,405 B2
(45) Date of Patent: Nov. 10, 2020

(54) MEDICAL IMAGE PROCESSING APPARATUS WITH AWARENESS OF TYPE OF SUBJECT PATTERN

(71) Applicant: KONICA MINOLTA, INC., Chiyoda-ku, Tokyo (JP)

(72) Inventor: Akihiro Kawabata, Hachioji (JP)

(73) Assignee: KONICA MINOLTA, INC., Tokyo (JP)

( * ) Notice: Subject to any disclaimer, the term of this patent is extended or adjusted under 35 U.S.C. 154(b) by 99 days.

(21) Appl. No.: 16/160,532

(22) Filed: Oct. 15, 2018

(65) Prior Publication Data
US 2019/0130564 A1    May 2, 2019

(30) Foreign Application Priority Data
Oct. 26, 2017    (JP) .................................. 2017-206756

(51) Int. Cl.
| | |
|---|---|
| G06T 7/00 | (2017.01) |
| A61B 8/08 | (2006.01) |
| A61B 8/00 | (2006.01) |
| G06T 7/11 | (2017.01) |
| G06K 9/68 | (2006.01) |
| A61B 8/06 | (2006.01) |

(52) U.S. Cl.
CPC .......... *G06T 7/0012* (2013.01); *A61B 8/5246* (2013.01); *A61B 8/06* (2013.01); *A61B 8/461* (2013.01); *A61B 8/488* (2013.01); *G06K 9/68* (2013.01); *G06T 7/11* (2017.01); *G06T 2207/10132* (2013.01)

(58) Field of Classification Search
CPC ...................... G06T 7/0012; G06T 7/11; G06T 2207/10132; A61B 8/5246; A61B 8/06; A61B 8/461; A61B 8/488; G06K 9/68
See application file for complete search history.

(56) References Cited

U.S. PATENT DOCUMENTS

| | | | |
|---|---|---|---|
| 2011/0188743 A1 | 8/2011 | Urushiya | |
| 2017/0360412 A1* | 12/2017 | Rothberg | A61B 8/52 |
| 2019/0236779 A1* | 8/2019 | Hattori | G01N 33/48 |

FOREIGN PATENT DOCUMENTS

| | | |
|---|---|---|
| JP | 2002360521 A | 12/2002 |
| JP | 2011156272 A | 8/2011 |

* cited by examiner

*Primary Examiner* — Pakee Fang
(74) *Attorney, Agent, or Firm* — Holtz, Holtz & Volek PC

(57) ABSTRACT

A medical image processing apparatus includes: a frame data generation part that generates frame data by scanning of a subject; and an image generation part that applies image processing on the generated frame data to generate medical image data, wherein the image generation part includes: a region dividing part that divides the generated frame data into frame data of a plurality of sub regions; a pattern classification part that classifies frame data of each of the sub regions in accordance with a pattern; a parameter selection part that selects a parameter for image processing for each sub region in accordance with a classification result of each of the sub regions; and an image processing execution part that applies image processing on frame data of each of the sub regions with use of a selected parameter of each a the sub regions.

18 Claims, 6 Drawing Sheets

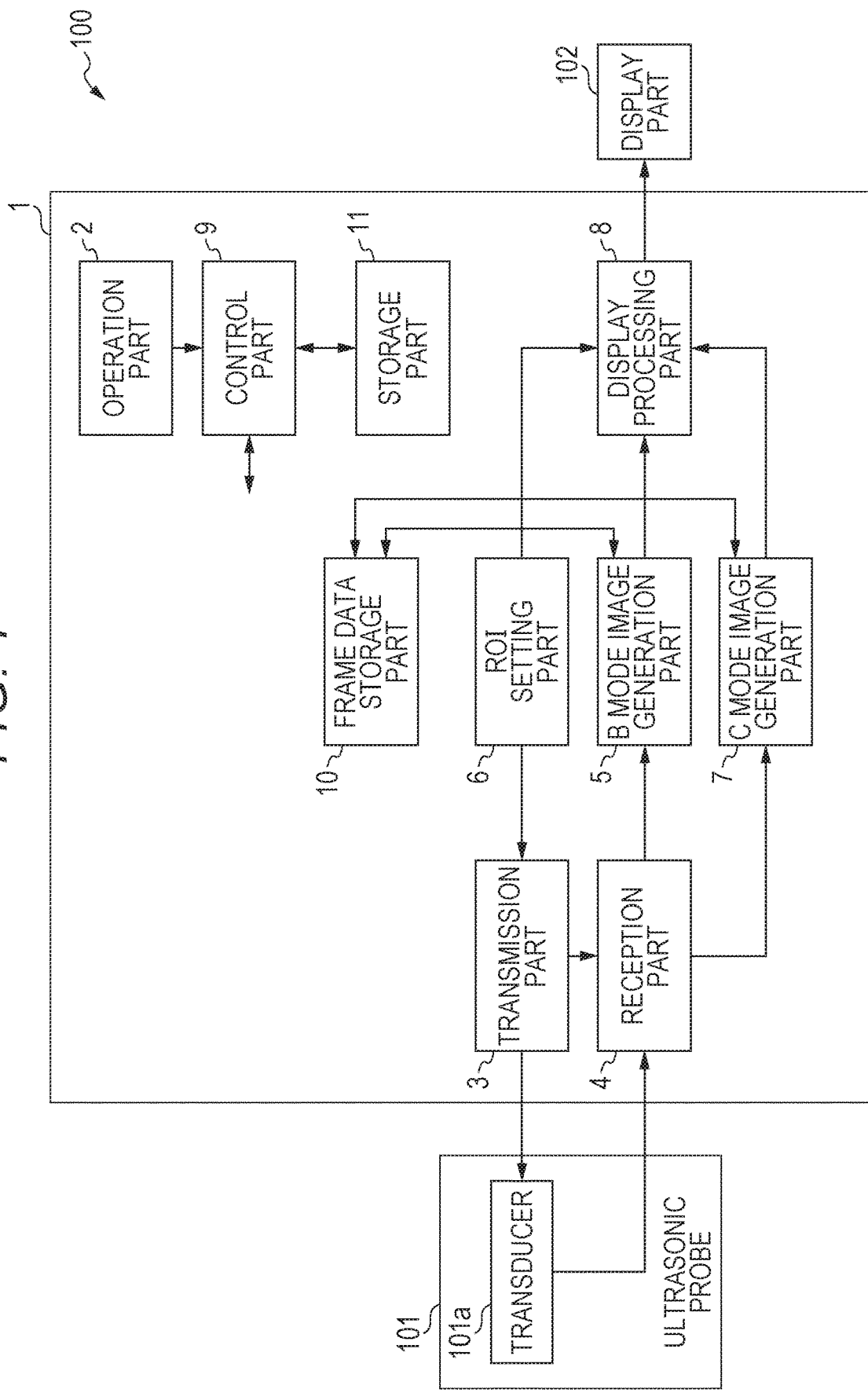

MEDICAL IMAGE PROCESSING APPARATUS WITH AWARENESS OF TYPE OF SUBJECT PATTERN

The entire disclosure of Japanese patent Application No. 2017-206756, filed on Oct. 26, 2017, is incorporated herein by reference in its entirety.

BACKGROUND

Technological Field

The present invention relates to a medical image processing apparatus.

Description of the Related Art

In ultrasonic diagnosis, a state of heartbeats or fetal movements is obtained by real-time display with a simple operation of simply applying an ultrasonic probe from a body surface, and inspection can be repeatedly conducted because of its high safety. An ultrasonic diagnostic apparatus is to image internal information of a subject as an ultrasonic image based on a reflected ultrasonic wave obtained by transmitting and receiving an ultrasonic wave toward inside the subject via the ultrasonic probe.

There is known an image processing apparatus that automatically discriminates a type (modality, image quality, and an imaged site) of medical images such as ultrasonic images, and executes image processing on the medical images with an algorithm suitable for the discriminated type (see JP 2002-360521 A).

There is also known an image processing apparatus that creates a tree structure in which imaging regions of medical images such as X-ray images are classified, identifies the imaging region in accordance with an identification unit corresponding to the tree structure, and applies image processing corresponding to the identified imaging region on the medical image (see JP 2011-156272 A).

The image processing on the ultrasonic image includes, for example, in common between a brightness mode (B mode) and a color flow mode (C mode) . . . smoothing, edge emphasis, persistence;

B mode specific . . . gradation conversion; and

C mode specific . . . noise cutting.

While an appropriate parameter varies depending on a target site of a subject, the above image processing discriminates or identifies the target site corresponding to the entire one frame in the conventional image processing apparatuses. For this reason, image processing is executed with a single parameter that is considered to be best suited in accordance with a setting input of the selected target site.

However, multiple sites may be included in one image. For example:

in a case of orthopedic . . . muscle, tendon, bone surface, nerve bundle, blood vessel, subcutaneous, and the like;

in a case of abdomen: liver, kidney, pancreas, diaphragm, blood vessel, and the like;

in a case of head and neck . . . vascular lumen, blood vessel wall, thyroid gland, nerve bundle, and the like; and in a case of heart . . . myocardium, endocardium, heart chamber, valve, blood vessel, and the like.

SUMMARY

An object of the present invention is to apply image processing with parameters suitable for individual sites when a plurality of sites are included in one image or a series of plural images.

To achieve the abovementioned object, according to an aspect of the present invention, a medical image processing apparatus reflecting one aspect of the present invention comprises: a frame data generation part that generates frame data by scanning of a subject; and an image generation part that applies image processing on the generated frame data to generate medical image data, wherein the image generation part comprises: a region dividing part that divides the generated frame data into frame data of a plurality of sub regions; a pattern classification part that classifies frame data of each of the sub regions in accordance with a pattern; a parameter selection part that selects a parameter for image processing for each sub region in accordance with a classification result of each of the sub regions; and an image processing execution part that applies image processing on frame data of each of the sub regions with use of a selected parameter of each of the sub regions.

BRIEF DESCRIPTION OF THE DRAWINGS

The advantages and features provided by one or more embodiments of the invention will become more fully understood from the detailed description given hereinbelow and the appended drawings which are given by way of illustration only, and thus are not intended as a definition of the limits of the present invention:

FIG. 1 is a schematic block diagram showing a configuration of an ultrasonic diagnostic apparatus according to an embodiment of the present invention;

DETAILED DESCRIPTION OF EMBODIMENTS

Figure 2A:
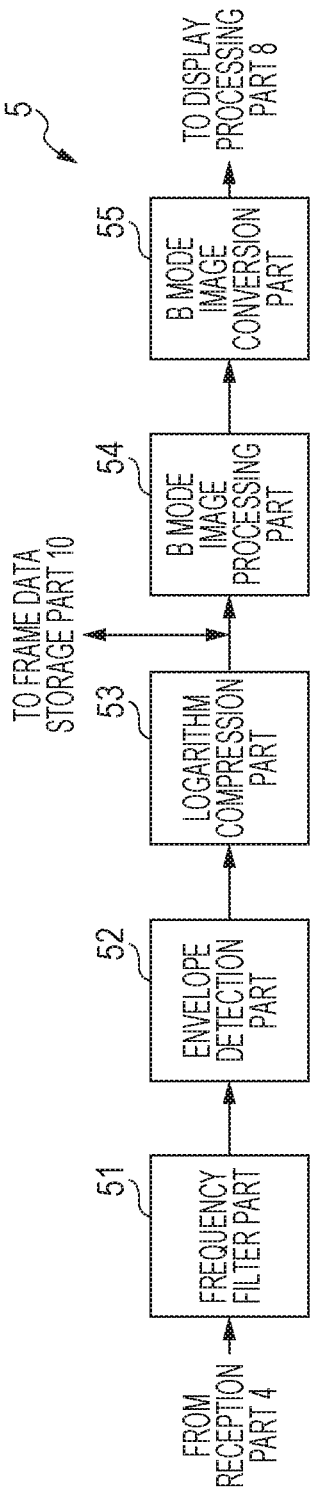
FIG. 2A is a schematic block diagram showing an internal configuration of a B mode image generation part according to the embodiment.

Hereinafter, one or more embodiments and modifications of the present invention will be described with reference to the drawings. However, the scope of the invention is not limited to the disclosed embodiments. In the following description, parts having a same function and a configuration are denoted by same reference numerals, and description thereof will be omitted.

Embodiment

Figure 2B:
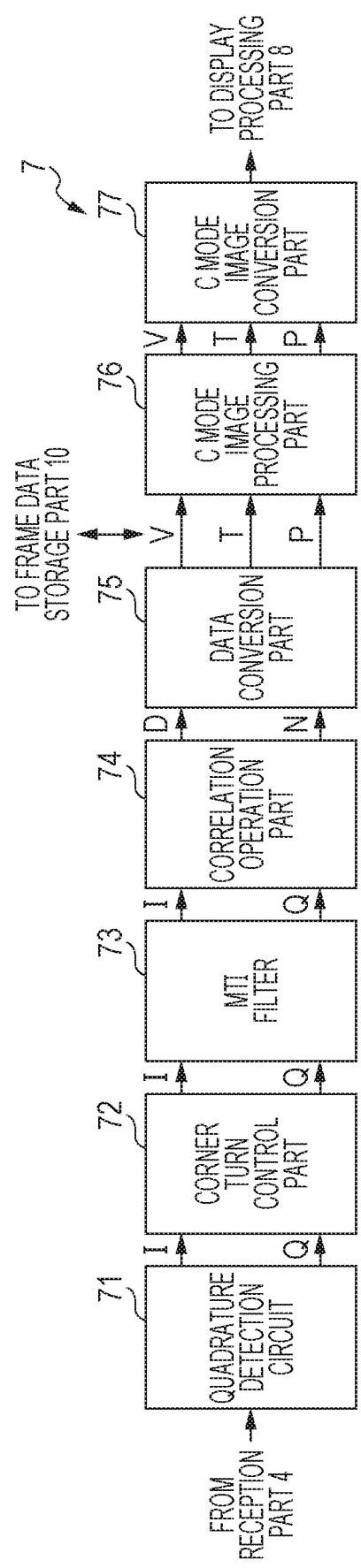
FIG. 2B is a schematic block diagram showing an internal configuration of a C mode image generation part according to the embodiment.
Figure 3A:
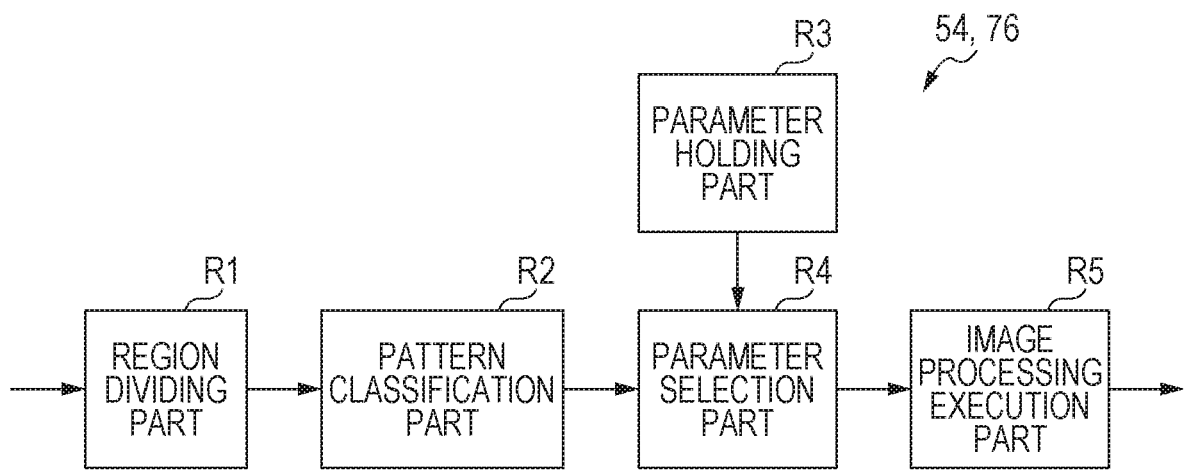
FIG. 3A is a schematic block diagram showing an internal configuration of a B mode image processing part or a C mode image processing part.
Figure 3B:
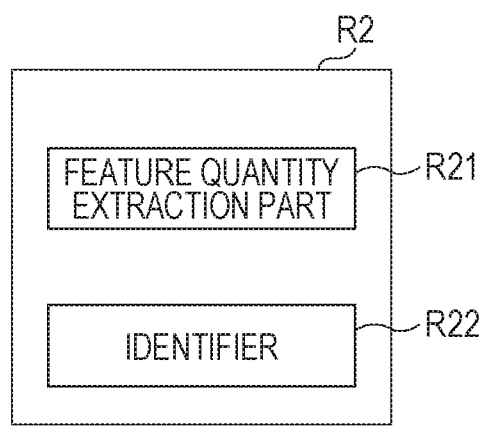
FIG. 3B is a schematic block diagram showing an internal configuration of a pattern classification part included in the B mode image processing part or the C mode image processing part.
Figure 4A:
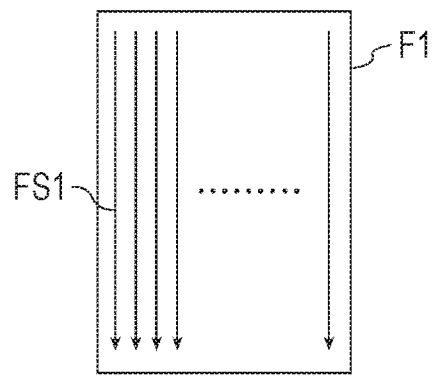
FIG. 4A is a view showing frame data before image conversion.
Figure 4B:
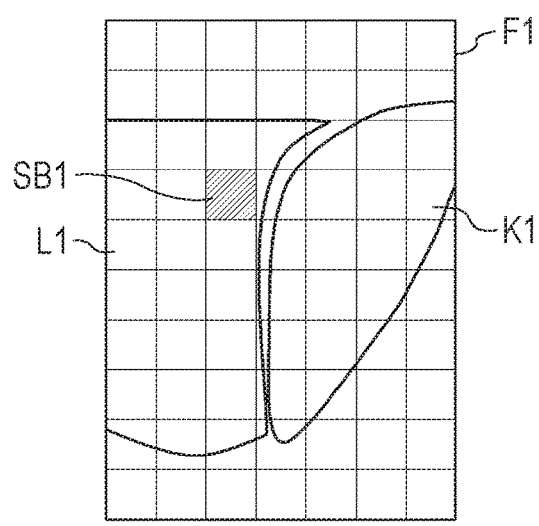
FIG. 4B is a view showing frame data divided into regions.
Figure 4C:
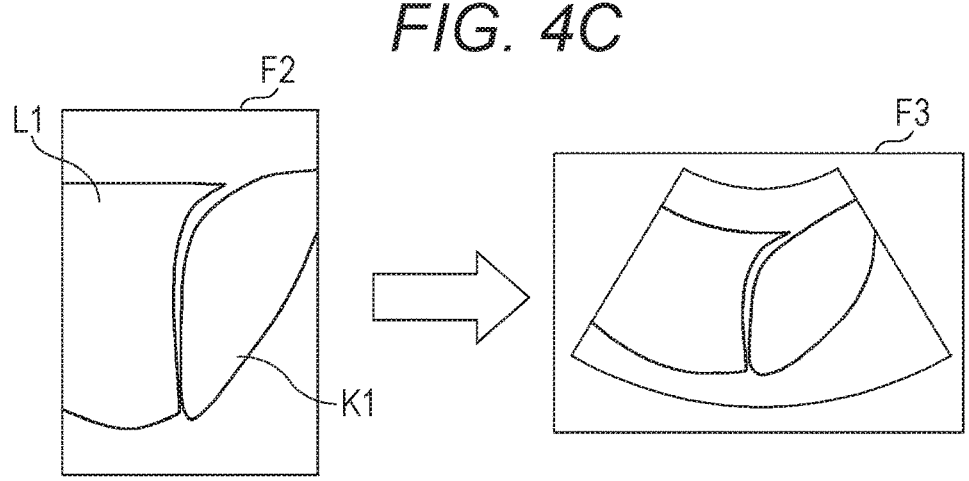
FIG. 4C is a view showing frame data subjected to image processing and B mode image data subjected to image conversion.

An embodiment according to the present invention will be described with reference to FIGS. 1 to 5. First, with reference to FIGS. 1 to 4C, an apparatus configuration of the present embodiment will be described. FIG. 1 is a schematic block diagram showing a configuration of an ultrasonic diagnostic apparatus 100 according to the present embodiment. FIG. 2A is a schematic block diagram showing an internal configuration of a B mode image generation part 5. FIG. 2B is a schematic block diagram showing an internal configuration of a C mode image generation part 7. FIG. 3A is a schematic block diagram showing an internal configuration of a B mode image processing part 54 or a C mode image processing part 76. FIG. 3B is a schematic block diagram showing an internal configuration of a pattern classification part R2 included in the B mode image processing part 54 or the C mode image processing part 76. FIG. 4A is a diagram showing frame data F1 before image conversion. FIG. 4B is a diagram showing the frame data F1 divided into regions. FIG. 4C is a view showing frame data F2 subjected to image processing and B mode image data F3 subjected to image conversion.

The ultrasonic diagnostic apparatus 100 of FIG. 1 as a medical image processing apparatus of the present embodiment shows a state where an ultrasonic probe 101 and a display part 102 are connected to an ultrasonic diagnostic apparatus body 1.

The ultrasonic diagnostic apparatus body 1 includes an operation part 2, a transmission part 3, a reception part 4, the B mode image generation part 5, a region of interest (ROI) setting part 6, the C mode image generation part 7, a display processing part 8, a control part 9, a frame data storage part 10, and a storage part 11.

The ultrasonic probe 101 has a plurality of transducers (piezoelectric transducer elements) 101a arranged in a one-dimensional direction. Each of the transducers 101a converts a drive signal (transmission electric signal) from the transmission part 3 described later into an ultrasonic wave, to generate an ultrasonic beam. Therefore, a user (operator) can irradiate an inside of a subject with the ultrasonic beam, by placing the ultrasonic probe 101 on a surface of the subject, which is a measurement object. Then, the ultrasonic probe 101 receives a reflected ultrasonic wave from the inside of the subject, converts the reflected ultrasonic wave into a reception electric signal by the plurality of transducers 101a, and supplies the reception electric signal to the reception part 4 described later.

In the present embodiment, a description is given as an example to the convex ultrasonic probe 101 in which the plurality of transducers 101a are arranged in a one-dimensional direction, but the present invention is not limited to this. For example, there may also be used a linear or sector ultrasonic probe 101 in which a plurality of transducers 101a are arranged in a one-dimensional direction, an ultrasonic probe 101 in which a plurality of transducers 101a are two-dimensionally arranged, an ultrasonic probe 101 in which a plurality of transducers 101a arranged in one-dimensional direction oscillate, and the like. Further, under control of the control part 9, the transmission part 3 can control an irradiation position and an irradiation direction of the ultrasonic beam transmitted by the ultrasonic probe 101, by selecting the transducer 101a to be used by the ultrasonic probe 101 and individually changing a timing to apply a voltage to the transducer 101a and a value of the voltage.

Further, the ultrasonic probe 101 may include a part of functions of the transmission part 3 and the reception part 4, which will be described later. For example, there is a configuration in which the ultrasonic probe 101 generates a drive signal in the ultrasonic probe 101 based on a control signal (hereinafter, referred to as "transmission control signal") that is outputted from the transmission part 3 and for generating a drive signal, converts this drive signal into an ultrasonic wave with the transducer 101a, converts the received reflected ultrasonic wave into a reception electric signal, and generates a reception signal described later based on the reception electric signal in the ultrasonic probe 101.

Although the ultrasonic probe 101 is generally electrically connected to the ultrasonic diagnostic apparatus body 1 via a cable, the present invention is not limited to this. For example, the ultrasonic probe 101 may be configured to transmit and receive a transmission signal and a reception signal to and from the ultrasonic diagnostic apparatus body 1 via a wireless communication such as an ultra-wide band (UWB). However, in a case of such a configuration, it is needless to say that the ultrasonic diagnostic apparatus 100 and the ultrasonic probe 101 are provided with a communication part capable of wireless communication.

Further, the ultrasonic probe 101 has a connector (not shown) connected to the ultrasonic diagnostic apparatus body 1 via a cable. This connector has a storage part that stores identification information indicating a type of the ultrasonic probe 101. Therefore, the control part 9 can read the information on the type of the ultrasonic probe 101 from the connector connected to the ultrasonic diagnostic apparatus body 1, via the reception part 4.

The display part 102 is a so-called monitor that displays image data outputted from the ultrasonic diagnostic apparatus body 1 (the display processing part 8). This embodiment shows a configuration in which the display part 102 is connected to the ultrasonic diagnostic apparatus 100. However, for example, the ultrasonic diagnostic apparatus body 1 and the display part 102 are integrally configured in a case of a so-called touch panel ultrasonic diagnostic apparatus in which the display part 102 and the operation part 2 to be described later are integrally configured and an operation of the operation part 2 is performed by touch operation on the display part 102. However, in the present application, even in the case where the ultrasonic diagnostic apparatus body 1 and the display part 102 are integrally formed, it is assumed that "the display part 102 is connected to the ultrasonic diagnostic apparatus body 1".

The operation part 2 receives an input from a user and outputs a command based on the user's input to the ultrasonic diagnostic apparatus 100, specifically the control part 9. The operation part 2 has a function of allowing the user to select a mode (hereinafter referred to as "B mode") to display a B mode image atone, or a mode (hereinafter referred to as "C mode") to superimpose and display a C mode (color flow mode) image on the B mode image. The operation part 2 also includes a function of specifying a position of the ROI on which the user is to display the C mode image on the B mode image. Further, the C mode image to be displayed includes a C mode image of display modes of a V mode to perform color display of a flow velocity and a direction of a blood flow with a blood flow velocity V as a blood flow signal indicating a state of a blood flow; a P mode to perform color display of a power of a blood flow with a power P of a blood flow as a blood flow signal; and a V-T mode to perform color display of a flow velocity and turbulence of a blood flow with the blood flow V and turbulence T as a blood flow signal. When receiving an input of the C mode from the user, the operation part 2 is to further receive an input of the display mode. The display mode of the C mode image may include a turbulence (T) mode, a directional power (dP) mode, and the like. As described above, the C mode includes a color Doppler mode (e.g., V mode, VT mode) and a power Doppler mode (e.g., P mode).

The transmission part 3 at least generates a drive signal and executes a transmission process to transmit an ultrasonic beam to the ultrasonic probe 101. As an example, the transmission part 3 drives the transducer 101*a* of the ultrasonic probe 101 by executing a transmission process of generating a drive signal for transmitting an ultrasonic beam from the ultrasonic probe 101 having the transducer 101*a*, and supplying a drive electric signal of high pressure generated at a predetermined timing to the ultrasonic probe 101 based on the drive signal. This allows the ultrasonic probe 101 to irradiate the subject as the measurement object with the ultrasonic beam by converting the drive electric signal into the ultrasonic wave.

Under control of the control part 9, the transmission part 3 executes a transmission process for displaying the C mode image in addition to the transmission process for displaying the B mode image when the C mode is on. For example, after supplying an electrical transmission signal for displaying the B mode image, the transmission part 3 repeatedly supplies a drive signal for quad signal processing (QSP) for displaying the C mode image for n times (e.g., n is 6 to 12) in a same direction (same line), for all directions (all lines) of the ROI set by the ROI setting part 6. However, the present invention is not limited to the driving signal for QSP. Further, at a time of the transmission process, the transmission part 3 specifies additional information indicating the transmission process for the B mode image or the transmission process for the C mode image, and supplies this additional information to the reception part 4.

Under control of the control part 9, the reception part 4 executes a reception process of generating a reception signal as an electrical radio frequency (RF) signal based on a reflected ultrasonic wave. For example, the reception part 4 receives a reflected ultrasonic wave with the ultrasonic probe 101, and generates a reception signal (sound ray data) by performing amplification, A/D conversion, and phasing addition of a reception electric signal, on the reception electric signal converted based on the reflected ultrasonic wave.

The reception part 4 acquires additional information from the transmission part 3, and supplies the reception signal to the B mode image generation part 5 when the acquired additional information is additional information for the B mode image, and supplies the reception signal to the C mode image generation part 7 when the acquired additional information is additional information for the C mode image. Hereinafter, a reception signal for generating the B mode image will be referred to as "B mode reception signal", and a reception signal for generating the C mode image will be referred to as "C mode reception signal".

In the present embodiment, the reception part 4 sorts whether a reception signal related to a generated image frame is for the B mode image or the C mode image to supply the sorted signal to each block, but the present invention is not limited to this. For example, the reception signal related to the generated image frame may be sorted by each of the B mode image generation part 5 and the C mode image generation part 7.

Under control of the control part 9, the B mode image generation part 5 generates B mode image data from the B mode reception signal inputted from the reception part 4, and outputs to the display processing part 8.

As shown in FIG. 2A, the B mode image generation part 5 includes a frequency filter part 51, an envelope detection part 52, a logarithm compression part 53, the B mode image processing part 54, and a B mode image conversion part 55. The frequency fitter part 51, the envelope detection part 52, and the logarithm compression part 53 function as a frame data generation part, while the B mode image processing part 54 and the B mode image conversion part 55 function as an image generation part.

The frequency filter part 51 is a so-called dynamic filter, and is a processing part that performs filtering to transmit a signal of a predetermined use frequency band through the B mode reception signal inputted from the reception part 4, under control of the control part 9. Under control of the control part 9, the envelope detection part 52 performs envelope detection on the B mode reception signal subjected to filtering and inputted from the frequency filter part 51.

Under control of the control part 9, the logarithm compression part 53 performs logarithmic compression on the B mode reception signal subjected to the envelope detection and inputted from the envelope detection part 52, and outputs the B mode reception signal (frame signal data as frame data) subjected to the logarithm compression to the frame data storage part 10. Under control of the control part 9, the B mode image processing part 54 reads B mode frame signal data for one frame subjected to logarithmic compression and stored in the frame data storage part 10, and executes image processing.

As shown in FIG. 3A, the B mode image processing part 54 has a region dividing part R1, the pattern classification part R2, a parameter holding part R3, a parameter selection part R4, and an image processing execution part R5.

Under control of the control part 9, the region dividing part R1 reads B mode frame signal data for one frame subjected to logarithmic compression and stored in the frame data storage part 10, and executes processing of spatially dividing the read B mode frame signal data for one frame into a plurality of sub regions. It is assumed that a size of each of the sub regions is, for example, a size of a pixel of a predetermined vertical length×a horizontal length set in advance.

For example, as shown in FIG. 4A, it is assumed a case where frame signal data FS as the B mode reception signal subjected to logarithm compression and inputted from the logarithm compression part 53 is collected to form one piece of the frame data F1. As shown in FIG. 4B, the region dividing part R1 divides the frame data F1 into sub regions SB1 having a predetermined size. It should be noted that an image of the frame data F1 includes, for example, images of a liver L1 and a kidney K1 of a subject.

Under control of the control part 9, the pattern classification part R2 classifies frame signal data of each of the sub regions inputted from the region dividing part R1, generates information on a type of tissue (site) of each of the sub regions or an image pattern indicating a feature of the tissue as a classification result, and outputs the frame signal data of each of the sub regions and the classification result to the parameter selection part R4.

As shown in FIG. 3B, the pattern classification part R2 has an identifier R22 that is based on mechanical learning, for example. In response to an input of frame signal data of each of the sub regions inputted from the region dividing part R1 or an input of a feature quantity of the frame signal data of each of the sub regions, the identifier R22 classifies frame signal data of each of the sub regions and outputs the classification result. The pattern classification part R2 has a feature quantity extraction part R21 that extracts a feature quantity from the frame signal data of each of the sub regions inputted from the region dividing part R1, and inputs to the identifier R22 in a case of inputting the feature quantity of the frame signal data of each of the sub regions to the identifier.

In response to, for example, an input of frame signal data of each of the sub regions or an input of a feature quantity of the frame signal data of each of the sub regions, the identifier R22 generates a classification result in accordance with a structure of a speckle pattern of the frame signal data of each of the sub regions. In this case, the feature quantity extraction part R21 extracts, for example, from the frame signal data of each of the sub regions, at least one feature vector of presence/absence, density, a particle size, and contrast of the speckle pattern as a feature quantity, and inputs to the identifier R22.

The identifier R22 may also be configured to classify the frame signal data of each of the sub regions with use of at least one of patient information or diagnostic use information, in addition to the frame signal data of each of the sub regions. The patient information is gender, race, age, height, weight, and the like of a patient as a subject. It is assumed that the patient information of each patient is stored in the storage part 11 in association with, for example, a patient ID of each patient. The diagnostic use information is at least one of preset (diagnosis site of the subject) information or information on a type of the ultrasonic probe 101.

In a case where a feature quantity of the frame signal data of each of the sub regions is inputted to the identifier R22, the identifier R22 is, for example, a discrimination analyzer, a support vector machine, or a neural network. When there is data (teacher data) divided into different classifications given in advance, and new data is inputted, the discrimination analyzer discriminates a classification of the new data on the premise of normal distribution for obtaining a criterion (discriminant function) for classification determination, based on an attribute value (feature quantity) of the new data. This attribute value of the new data is to be the feature quantity of the frame signal data of each of the sub regions extracted by the feature quantity extraction part R21. For example, it is assumed that the criterion (discriminant function) for classification determination is set in a memory (not shown) of the identifier R22 in advance and can be updated.

A support vector machine is one of pattern recognition models using supervised learning, and a two-class pattern identifier is configured with use of a linear input element. The support vector machine learns, from a training sample, a parameter of the linear input element with a criterion (hyperplane separation theorem) of determining a margin-maximizing hyperplane that maximizes a distance between individual data points, and classifies the linear input element with margin maximizing hyperplane. This linear input element is to be the feature quantity of the frame signal data of each of the sub regions extracted by the feature quantity extraction part R21. For example, it is assumed that the data of the margin-maximizing hyperplane based on the training sample is set in the memory (not shown) of the identifier R22 in advance and can also be updated.

The neural network is a model in which artificial neurons (nodes) forming a network by synaptic connections change a connection strength of synapses by learning, and has problem solving ability. The neural network is configured by a node of each layer of an input layer→an intermediate layer→an output layer, and by weight indicating a strength of connection between the individual nodes. When there are a plurality of intermediate layers, it is called deep learning. Input information to the node of the input layer is to be the feature quantity of the frame signal data of each of the sub regions extracted by the feature quantity extraction part R21. Output information of the node of the output layer is to be a classification result. Further, in the neural network, connection weight between the nodes is adjusted such that a value of the output node approaches the teacher data, which is a correct solution. For example, it is assumed that data of the connection weight between the nodes is set in the memory (not shown) of the identifier R22 in advance and can be updated.

In a case where frame signal data of each of the sub regions is inputted to the identifier R22, the identifier R22 is, for example, a convolutional neural network. The convolutional neural network is a neural network having a convolutional filter (convolutional layer) as an intermediate layer that calculates a match over the entire input image with use of an image piece (called a feature) of a size smaller than that of the input image, and performs filtering by calculating the number of matches. Therefore, the input information to the node of the input layer is to be the frame signal data of each of the sub regions. Here, it is assumed that the identifier R22 has a convolutional filter corresponding to a speckle pattern. Such a convolutional filter can be constructed by performing mechanical learning in advance with use of a sub region of learning frame data having a speckle pattern. Output information of the node of the output layer is to be a classification result. For example, it is assumed that data of the connection weight between the nodes is set in the memory (not shown) of the identifier R22 in advance and can be updated.

The parameter holding part R3 is a memory to store information, and stores a parameter for image processing for the B mode corresponding to information on a type of tissue or an image pattern as the classification result of the pattern classification part R2. Under control of the control part 9, the parameter selection part R4 selects a parameter for image processing for the B mode corresponding to the classification result out of the frame signal data of each of the sub regions and the classification result inputted from the pattern classification part R2, reads the selected parameter from the parameter holding part R3, and outputs the frame signal data and the parameter of each of the sub regions to the image processing execution part R5.

The image processing for the B mode image is image processing including, for example, at least one of smoothing (smoothing filter), edge emphasis, persistence, or gradation conversion. The smoothing is a process of smoothing frame data by obtaining a weighted average of peripheral data of target sample data (pixels in a case of images). This is also called a smoothing filter, and weight of the weighted average is to be namely a filter coefficient. When Gaussian is used instead of the weight, it is called Gaussian filter. Parameters for the smoothing are weight (filter coefficient) and a kernel size (filter size). Parameters for the Gaussian filter are a standard deviation of weight and a kernel size (filter size).

The edge emphasis is also referred to as a sharpening filter, and is a process of emphasizing an outline (change) of frame data (image). A typical algorithm includes unsharp masking. The unsharp masking is a process of adding an edge component (a value obtained by multiplying a Laplacian filter result by weight) to original data (an original image). Parameters for the edge enhancement are a filter coefficient and a kernel size (filter size). Parameters for the unsharp masking are a coefficient of the edge component (Laplacian filter result) and a kernel size (mask size).

The persistence is a process of smoothing a change in an image and providing an afterimage effect by mutually filtering pieces of sample data at a same position in consecutive frames. An example of a case where the persistence is configured by an infinite impulse response (IIR) is represented by the following Equation (0). Vout=(1−C(Vout, Vout−1)) Vcurrent+C(Vout, Vout−1)×Vout−1 . . . (0) Here, Vout: a value of a persistence processing result of a current frame (V is the initial letter of Value) Vcurrent: a sample value of the current frame (same as above), Vout−1: a value of a persistence processing result of a previous frame (same as above), and C (Vout, Vout−1): a persistence coefficient (C is the initial letter of Coefficient), and the value is determined in accordance with Vout and Vout−1 (a function of Vout and Vout−1). A parameter for the persistence is a persistence coefficient or a function that determines the persistence coefficient.

The gradation conversion is a process of converting a brightness value of frame data (image) in accordance with a predetermined gradation conversion curve, and includes contrast adjustment and gamma correction. A parameter for the gradation conversion is a gradation conversion table (look up table: LUT). A parameter for the gamma correction is a gamma correction value.

The parameter selection part R4 selects a parameter for image processing selected and set in advance in accordance with information on a type of tissue or an image pattern. However, for example, when a user (examiner (e.g., doctor, technician)) has inputted a type of a parameter to be used for each information on a type of tissue or an image pattern via the operation part 2, the parameter selection part R4 selects a value of the parameter of the type of operation input. A parameter for image processing is selected and set for each sub region.

Under control of the control part 9, the image processing execution part R5 uses the parameter for the image processing inputted from the parameter selection part R4, to apply the image processing to the frame signal data of each of the sub regions inputted from the parameter selection part R4.

Under control of the control part 9, the B mode image conversion part 55 generates B mode image data and outputs to the display processing part 8 by performing coordinate transformation as a digital scan converter (DSC) on the frame signal data subjected to image processing and inputted from the B mode image processing part 54 (image processing execution part R5), and adjusting a dynamic range and a gain to perform luminance conversion (gray scale mapping). As shown in FIG. 4C, for example, the B mode image conversion part 55 converts the frame data F2 obtained by image processing of the frame data F1 with the image processing execution part R5 into convex B mode image data F3.

Returning to FIG. 1, under control of the control part 9, the ROI setting part 6 outputs setting information of the ROI to the transmission part 3 and the display processing part 8, in accordance with the setting information of the ROI inputted from the user via the operation part 2.

Under control of the control part 9, the C mode image generation part 7 generates C mode image data in accordance with the C mode reception signal inputted from the reception part 4, and outputs to the display processing part 8. Here, referring to FIG. 2B, an internal configuration of the C mode image generation part 7 will be described. As shown in FIG. 2B, the C mode image generation part 7 includes a quadrature detection circuit 71, a corner turn control part 72, a moving target indication (MTI) filter 73, a correlation operation part 74, a data conversion part 75, the C mode image processing part 76, and a C mode image conversion part 77. The quadrature detection circuit 71, the corner turn control part 72, the MTI filter 73, the correlation operation part 74, and the data conversion part 75 function as a frame data generation part, while the C mode image processing part 76 and the C mode image conversion part 77 function as an image generation part.

Under control of the control part 9, the quadrature detection circuit 71 performs quadrature detection on the C mode reception signal inputted from the reception part 4, to calculate a phase difference between the acquired C mode reception signal and a reference signal and acquire complex Doppler signals I and Q.

Under control of the control part 9, the corner turn control part 72 arranges the Doppler signals I and Q inputted from the quadrature detection circuit 71 in a depth direction from the ultrasonic probe 101 to the subject and an ensemble direction of a repetition number n of transmission and reception of an ultrasonic wave for each identical sound line (line), stores the Doppler signals I and Q in a memory (not shown), and reads the Doppler signals I and Q in the ensemble direction for each depth.

In addition to a signal component of a blood flow required for C mode image generation, information such as unnecessary blood vessel walls or tissues (clutter components) is mixed in the reception signal (Doppler signals I and Q). Under control of the control part 9, the MTI filter 73 performs filtering on the Doppler signals I and Q outputted from the corner turn control part 72 to remove clutter components.

Under control of the control part 9, the correlation operation part 74 calculates a real part D and an imaginary part N of a mean value S (a mean value of a phase difference vector) of autocorrelation operation of the Doppler signal from the Doppler signals I and Q (complex Doppler signal z) filtered by the MTI filter 73 with the following Equation (1).

[Equation 1]

$$S = \sum_{k=1}^{n-1} z_k^* \cdot z_{k+1} = D + jN \quad (1)$$

Under control of the control part 9, the data conversion part 75 calculates the blood flow velocity V, the power P, and the turbulence T from the Doppler signals I and Q filtered by the MTI filter 73 and from the real part D and the imaginary part N of the mean value S of the autocorrelation operation of the Doppler signal. More specifically, the data conversion part 75 calculates the blood flow velocity V from the real part D and the imaginary part N of the mean value S of the autocorrelation operation of the Doppler signal with the following Equation (2).

[Equation 2]

$$V = \tan^{-1}\frac{N}{D} \quad (2)$$

In addition, the data conversion part 75 calculates the power P as the mean value of intensity of the Doppler signal from the Doppler signals I and Q (complex Doppler signal z) with the following Equation (3).

[Equation 3]

$$P = \frac{1}{n}\sum_{k=1}^{n} |z_k|^2 \quad (3)$$

Further, the data conversion part 75 calculates the turbulence T as a ratio of a magnitude of a phase difference vector to the power (however, a value obtained by subtracting from 1 and inverting a magnitude) from the Doppler signals I and Q (complex Doppler signal z) with the following Equation (4).

[Equation 4]

$$T = 1 - \frac{\sqrt{D^2 + N^2}}{P} \quad (4)$$

The data conversion part 75 outputs the calculated blood flow velocity V, power P, and turbulence (assumed to be frame signal data as frame data) to the frame data storage part 10.

Under control of the control part 9, the C mode image processing part 76 reads C mode frame signal data for one frame or latest consecutive plural frames stored in the frame data storage part 10, and executes image processing.

As shown in FIGS. 3A and 3B, the C mode image processing part 76 has a region dividing part R1, a pattern classification part R2, a parameter holding part R3, a parameter selection part R4, and an image processing execution part R5.

Under control of the control part 9, the region dividing part R1 reads C mode frame signal data for the ROI for one frame or latest consecutive plural frames stored in the frame data storage part 10, and executes processing of spatially dividing the read C mode frame signal data for one frame or consecutive plural frames into a plurality of sub regions.

Under control of the control part 9, the pattern classification part R2 classifies frame signal data for one or plural frames of each of the sub regions inputted from the region dividing part R1, generates information on a type of tissue (site) of each of the sub regions or an image pattern indicating a feature of the tissue as a classification result, and outputs the frame signal data of each of the sub regions for one frame and a classification result to the parameter selection part R4.

As shown in FIG. 3B, the pattern classification part R2 has an identifier R22 that is based on mechanical learning, for example. In response to an input of frame signal data for one or plural frames of each of the sub regions inputted from the region dividing part R1 or an input of a feature quantity of the frame signal data of each of the sub regions, the identifier R22 classifies frame signal data of each of the sub regions and outputs the classification result. The pattern classification part R2 has the feature quantity extraction part R21 that extracts a feature quantity from the frame signal data of each of the sub regions for one or plural frames inputted from the region dividing part R1, and inputs to the identifier R22 in a case of inputting the feature quantity of the frame signal data of each of the sub regions to the identifier R22.

In response to, for example, an input of frame signal data for one or plural frames of each of the sub regions or an input of a feature quantity of the frame signal data of each of the sub regions, the identifier R22 generates a classification result in accordance with a pattern of a blood flow and noise of frame signal data of each of the sub regions for the one frame. In addition to the component of the blood flow, the C mode frame signal data also includes noise accompanying a movement of tissue, which is called clutter noise or motion noise.

In inputting a feature quantity, the feature quantity extraction part R21 extracts as a feature quantity, for example, from frame signal data of each of the sub regions for one frame, at least one feature vector of a thickness and a direction of a blood flow; and presence/absence, density; and a particle size of noise, and inputs the feature vector to the identifier R22. Further, the feature quantity extraction part R21 extracts as a feature quantity, for example, from the frame signal data of each of the sub regions for consecutive plural frames, at least one feature vector of: a thickness, a direction, and pulsatility of a blood flow; and presence/absence, density, a particle size, and interframe variation of noise, and inputs the feature vector to the identifier R22. The pulsatility is a property of a repeated motion with periodic contraction and relaxation of internal organs, and varies, for example, among the aorta and the carotid artery, the thyroid and fingers, and the veins. For the interframe variation, noise that randomly appears and disappears should be erased, and for example, a parameter that causes a strong effect of a noise cut process to be described later is selected.

The identifier R22 may also be configured to classify the frame signal data of each of the sub regions with use of at least one of patient information or diagnostic use information, in addition to the frame signal data of each of the sub regions.

In a case where a feature quantity of the frame signal data of each of the sub regions is inputted, the identifier R22 is, for example, a discrimination analyzer, a support vector machine, or a neural network.

In a case where frame signal data of each of the sub regions is inputted, the identifier R22 is, for example, a convolutional neural network. The input information to the node of the input layer is to be frame signal data of each of the sub regions for one or consecutive plural frames. Further, it is assumed that the identifier R22 has a convolutional filter corresponding to a pattern of a blood flow and noise. Such a convolutional filter can, be constructed by performing mechanical learning in advance with use of a sub region of learning frame data having a pattern of a blood flow and noise. Output information of the node of the output layer is to be a classification result. For example, it is assumed that data of the connection weight between the nodes is set in the memory (not shown) of the identifier R22 in advance and can be updated.

The parameter holding part R3 is a memory to store information, and stores a parameter for image processing for mode C mode corresponding to information on a type of tissue or an image pattern as a classification result of the pattern classification part R2. Under control of the control part 9, the parameter selection part R4 selects a parameter for image processing for mode C mode corresponding to the classification result out of the frame signal data of each of the sub regions and the classification result inputted from the pattern classification part R2, reads the selected parameter from the parameter holding part R3, and outputs the frame signal data and the parameter of each of the sub regions to the image processing execution part R5.

The image processing for the C mode image is image processing including, for example, at least one of smoothing, edge emphasis, persistence, or a noise cut process. The noise cut process is a process of removing noise, and there are methods such as a median filter, an isolated point removal, and a threshold process. The median filter is a process of taking a median value of peripheral data of a target sample data (pixels in a case of images), and helps removing noise that is significantly different from the peripheral data. A parameter for the median filter is a kernel size (filter size).

The isolated point removal is a process of checking whether a number of non-zero data around the target sample data (pixels in a case of an image) is equal to or greater than a predetermined threshold value, and removing the data if it is less than the threshold value. A parameter for the isolated point removal is a threshold of the number of peripheral non-zero data.

The threshold process is a so-called keyhole filter, which is a process of comparing target sample data (the blood flow velocity V and the power P in the C mode) with a predetermined threshold value, and regarding as clutter noise when the blood flow velocity V is less than the threshold value and regarding as background noise when the power P is less than the threshold value, to remove the data. A parameter for the threshold process is a threshold of the blood flow velocity V and the power P.

The parameter selection part R4 selects a parameter for image processing selected and set in advance in accordance with a type of tissue or information of the image pattern. However, for example, when a user has inputted a type of a parameter to be used for each information on a type of tissue or an image pattern via the operation part 2, the parameter selection part R4 selects a value of the parameter of the type of operation input. A parameter for image processing is selected and set for each sub region.

Under control of the control part 9, the image processing execution part R5 uses the parameter liar the image processing inputted from the parameter selection part R4, to apply the image processing to the frame signal data of each of the sub regions inputted from the parameter selection part R4.

Under control of the control part 9, the C mode image conversion part 77 generates C mode image data of the ROI in a specification mode specified by the user of the C mode and outputs to the display processing part 8, by performing coordinate transformation as a DSC on the frame signal data subjected to image processing and inputted from the C mode image processing part 76 (image processing execution part R5), and performing color mapping.

The display processing part 8 constructs display image data to be displayed on the display part 102, and executes processing of displaying the display image data on the display part 102. In particular, when the B mode is selected, the display processing part 8 executes processing of including the B mode image of the B mode image data generated by the B mode image generation part 5 as an ultrasonic image in the display image data. In addition, when the C mode is selected, the display processing part 8 executes processing of generating, as ultrasonic image, composite image data obtained by superimposing the C mode image of the C mode image data, generated by the C mode image generation part 7 on a selected position of the ROI on the B mode image generated by the B mode image generation part 5, and including this in the display image data.

The control part 9 includes, for example, a central processing unit (CPU), a read only memory (ROM), and a random access memory (RAM), reads various processing programs such as a system program stored in the ROM, develops them in the RAM, and controls an operation of each part of the ultrasonic diagnostic apparatus 100 in accordance with the developed program. The RAM forms a work area for temporarily storing various programs to be executed by the CPU and data relating to these programs. The ROM is configured by a nonvolatile memory such as a semiconductor, and stores a system program for the ultrasonic diagnostic apparatus 100 and various processing programs such as an initial setting program and an ultrasonic diagnostic program that can, be executed on the system program, and stores various data and the like. These programs are stored in a form of computer-readable program codes, and the CPU sequentially executes operations in accordance with the program codes. In particular, it is assumed that the ROM stores a C mode image display program.

The storage part 11 is configured by a large capacity recording medium such as a hard disk drive (HDD), for example, and stores ultrasonic image data (B mode image data, C mode composite image data, and frame signal data) and the like. It is also assumed that the storage part 11 stores patient information associated with the patient ID.

For each part of the ultrasonic diagnostic apparatus 100, part or all of functions of the respective functional blocks can be realized as a hardware circuit such as an integrated circuit. The integrated circuit is, for example, a large scale integration (LSI). The LSI may be referred to as an integrated circuit (IC), a system LSI, a super LSI, or an ultra. LSI depending on a degree of integration. Further, a method for circuit integration is not limited to the LSI, but may be realized by a dedicated circuit or a general-purpose processor, and there may be used a reconfigurable processor capable of reconfiguring connection and setting of circuit cells in a field programmable gate array (FPGA) or an LSI. Further, part or all of functions of the respective functional blocks may be executed by software. In this case, this software is stored in one or more storage media such as a ROM, an optical disk, and a hard disk, and this software is executed by an arithmetic processor.

Figure 5:
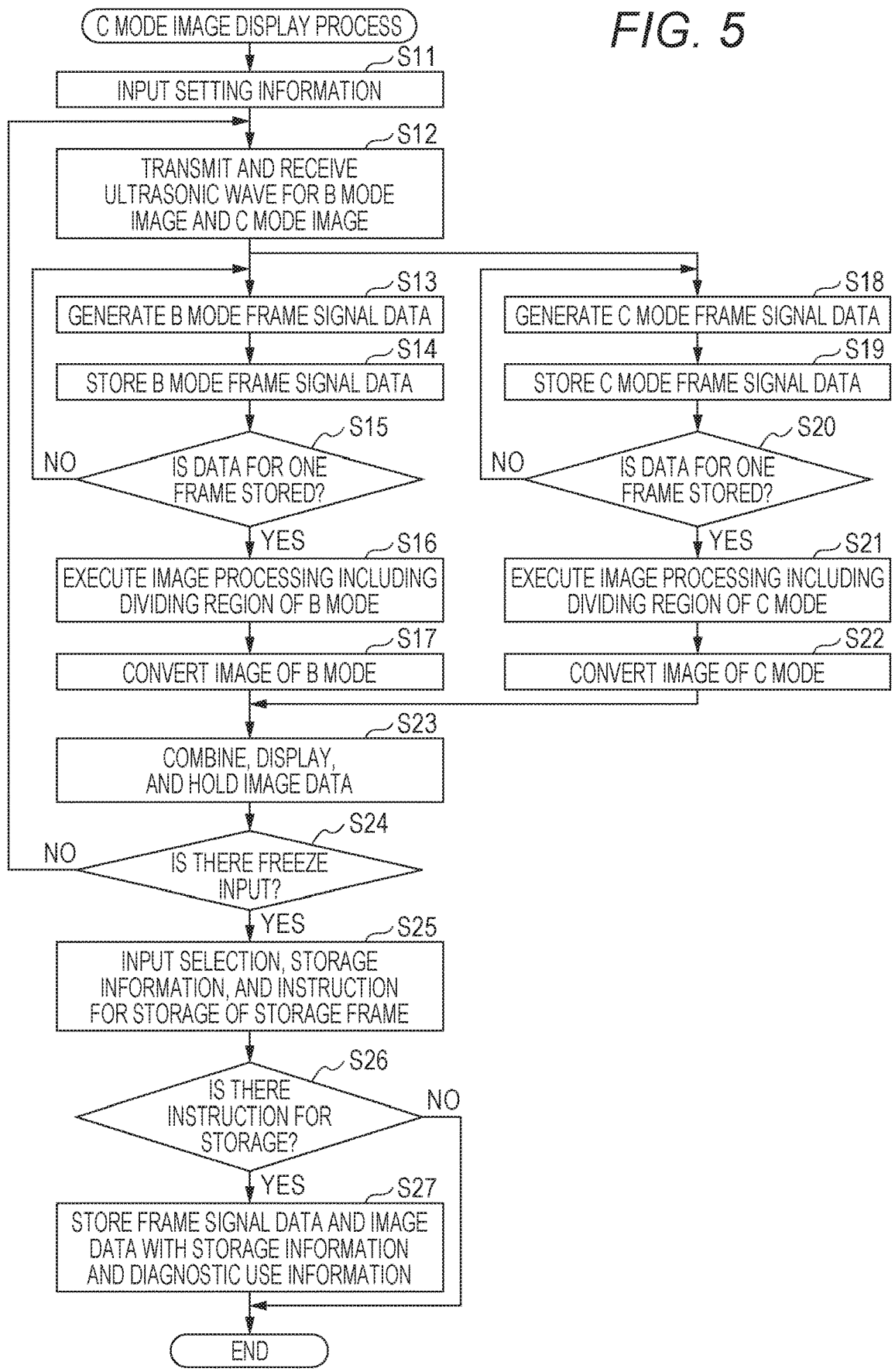
FIG. 5 is a flowchart showing a C mode image display process.

Next, with reference to FIG. 5, an operation of the ultrasonic diagnostic apparatus 100 will be described. FIG. 5 is a flowchart showing a C mode image display process.

The C mode image display process of FIG. 5 will be described. The C mode image display process is a process of dividing frame signal data of a B mode image and a C mode image into regions, applying appropriate image processing on each of the sub regions to convert the image, and combining the obtained B mode image data and C mode image data to display and save the data. It is assumed that, in advance, a patient as the subject has entered a diagnosis room installed with the ultrasonic diagnostic apparatus 100 in a medical institution and lain down on a bed or the like, a user as the examiner is in a state of being able to operate the ultrasonic diagnostic apparatus 100, and preparation for ultrasonic examination has been completed.

In the ultrasonic diagnostic apparatus 100, for example, with an input of an instruction to execute the C mode image display process from the user via the operation part 2 as a trigger, the control part 9 executes the C mode image display process in accordance with the C mode image display program read from the internal memory and appropriately developed in the RAM.

First, the control part 9 receives an input of various setting information from the user via the operation part 2, and acquires type information of the ultrasonic probe 101 from the connector of the ultrasonic probe 101 as setting information (step S11). The setting information to be inputted through operation includes; a patient ID of a patient to be inspected; selection information of a specification mode such as the V mode in the C mode; selection information of a type of a parameter for image processing to be used; preset information (diagnosis site of the subject); and specification information of the ROI. When the patient ID is inputted, the control part 9 reads and acquires patient information corresponding to the inputted patient ID from the storage part 11.

Next, the user appropriately applies the ultrasonic probe 101 to the skin of the examination target site of the subject. Then, the control part 9 controls the ROI setting part 6 in accordance with the specification information of the ROI, causes the transmission part 3 to generate a drive signal for the B mode image and a drive signal for the C mode image corresponding to the ROI, causes the ultrasonic probe 101 to transmit a transmission ultrasonic wave in accordance with a drive signal, and causes the reception part 4 to generate a B mode reception signal and a C mode reception signal based on a reception signal generated by the ultrasonic probe 101 upon receiving the reflected ultrasonic wave of the transmission ultrasonic wave (step S12).

Next, the control part 9 controls the frequency filter part 51, the envelope detection part 52, and the logarithm compression part 53 to generate B mode frame signal data based on the B mode reception signal generated in step S12 (step S13). Then, the control part 9 stores the B mode frame signal data generated in step S13 in the frame data storage part 10 (step S14).

Next, the control part 9 determines whether the B mode frame signal data for one frame has been stored in the frame data storage part 10 through a latest loop of steps S13 to S15 (step S15). When the B mode frame signal data for one frame has not been stored (step S15; NO), the process proceeds to step S13. When the B mode frame signal data for one frame has been stored (step S15; YES), the control part 9 controls the B mode image processing part 54 to read the B mode frame signal data for one frame from the frame data storage part 10, and execute image processing using setting information inputted in step S11, on the read frame signal data for one frame (step S16).

Then, the control part 9 controls the B mode image conversion part 55 to perform image conversion on the B mode frame signal data for one frame subjected to the image processing and generated in step S16, and generate B mode image data (step S17).

After step S12, the control part 9 controls the quadrature detection circuit 71, the corner turn control part 72, the MTI filter 73, the correlation operation part 74, and the data conversion part 75 to generate C mode frame signal data based on the C mode reception signal generated in step S12 (step S18). Then, the control part 9 stores the C mode frame signal data generated in step S18 in the frame data storage part 10 (step S19).

Next, the control part 9 determines whether the C mode frame signal data for one frame has been stored in the frame data storage part 10 through a latest loop of steps S18 to S20 (step S20). When the C mode frame signal data for one frame has not been stored (step S20; NO), the process proceeds to step S18. When the C mode frame signal data for one frame has been stored (step S20; YES), the control part 9 controls the C mode image processing part 76 to read C mode frame signal data for one frame or latest consecutive plural frames from the frame data storage part 10, and execute image processing on frame signal data for one frame with use of the read frame signal data for one or plural frames and the setting information inputted in step S11 (step S21). In step S21, C mode frame signal data for one frame subjected to image processing is generated.

Then, the control part 9 controls the C mode image conversion part 77 to perform image conversion on the C mode frame signal data for one frame subjected to the image processing and generated in step S21, and generate C mode image data (step S22).

Then, the control part 9 controls the display processing part 8 to combine the B mode image data for one frame generated in step S17 and the C mode image data for one frame generated in step S22 to generate and display composite image data on the display part 102, and cause a cine-memory (not shown) to hold the composite image data (step S23). The cine-memory is, for example, a memory of a first-in first-out system, which holds the latest ultrasonic image data of a predetermined number of frames.

Then, the control part 9 receives a freeze input from the user via the operation part 2, and determines whether there is a freeze input or not (step S24). When there is no freeze input (step S24; NO), the process proceeds to step S12. When there is a freeze input (step S24; YES), the control part 9 receives an input of selection information, storage information, and an instruction for storage of a storage frame among a predetermined number of frozen frames, from the user via the operation part 2 (step S25). The storage information is text annotation information, body mark information, or the like to be added to image data (composite image data) for storage.

Then, the control part 9 determines whether the instruction for storage has been inputted in step S24 (step S26). When the instruction for storage is not inputted (step S26; NO), the C mode image display process is terminated. When the instruction for storage is inputted (step S26; YES), the control part 9 reads the composite image data of the frame selected in step S25 from the cine-memory, combines the storage information inputted in step S25 with the composite image data, reads B mode and C mode frame signal data that corresponds to the composite image data of the frame from the frame data storage part 10, saves (stores) the B mode and C mode frame signal data, the storage information, and the diagnostic use information that has been inputted in step S11, in the storage part 11 in association with the composite image data (step S27), and terminates the C mode image display process.

Regarding a flow of the B mode image display process, among the steps in the C mode image display process, an ultrasonic wave for the B mode image is transmitted and received in step S12, steps S18 to S22 are not executed, the B mode image data is displayed and held in step S23, and the B mode frame signal data and the storage information are stored in the storage part 11 in association with the B image data subjected to the image processing in step S27.

Among the information stored in the storage part 11, the B mode frame signal data or the B mode and C mode frame signal data is used, along with the storage information, as learning data for the identifier of the pattern classification part R2 of the B mode image processing part 54 and the C mode image processing part 76. For example, in the ultrasonic diagnostic apparatus 100, the B mode frame signal data, or the B mode and C mode frame signal data and the storage information stored in the storage part 11 are transmitted by the control part 9 to a server communicatively connected via a communication part (not shown), to be used for adjustment of the identifier of the pattern classification part R2 (e.g., adjustment of teacher data of a discriminant analyzer, data of a margin-maximizing hyperplane of a support vector machine, or data of a connection weight between nodes in a neural network). For example, adjustment data of the identifier after adjustment may be set in the identifier of the pattern classification part R2.

Further, the storage part 11 is a built-in storage of the ultrasonic diagnostic apparatus 100, but the present invention is not limited to this. The storage part 11 may be an externally attached storage or an external storage network-connected to the ultrasonic diagnostic apparatus 100. In either configuration, the B mode frame signal data, or the B mode and C mode frame signal data and the storage information stored in the storage part 11 can be used for adjustment of the identifier of the pattern classification part R2.

As described above, according to the present embodiment, the ultrasonic diagnostic apparatus 100 includes: the transmission part 3 that generates a drive signal and inputs the generated drive signal to the ultrasonic probe 101 that transmits a transmission ultrasonic wave to the subject in accordance with a drive signal and receives a reflected ultrasonic wave; the reception part 4 that generates a reception signal from an electric signal generated by the ultrasonic probe 101; the frequency filter part 51, the envelope detection part 52, the logarithm compression part 53, the quadrature detection circuit 71, the corner turn control part 72, the MTI filter 73, the correlation operation part 74, and the data conversion part 75 that generate frame signal data by scanning of the subject; and the image generation part (the B mode image processing part 54, the B mode image conversion part 55, the C mode image processing part 76, the C mode image conversion part 77) that generates ultrasonic image data by applying image processing on the generated frame signal data. The image generation part includes: the region dividing part R1 that divides the generated frame signal data into frame signal data of a plurality of sub regions; the pattern classification part R2 that classifies frame signal data of each of the sub regions in accordance with a pattern; the parameter selection part R4 that selects a parameter for image processing in accordance with a classification result of each of the sub regions; and the image processing execution part R5 that applies image processing on frame signal data of each of the sub regions with use of the selected parameter of each of the sub regions and generates frame signal data subjected to image processing.

Therefore, when a plurality of sites are included in one image or in a series of plural ultrasonic images, image processing can be applied with a parameter suitable for each site by applying image processing on the frame signal data of each of the sub regions with a parameter of each of the sub regions.

The pattern classification part R2 classifies frame signal data of each of the sub regions in accordance with a type of tissue of the subject. Therefore, image processing can, be applied with a parameter suitable for each site of each type of tissue of the subject.

Further, the pattern classification part R2 has an identifier R22 that is based on mechanical learning and classifies frame signal data of each of the sub regions in accordance with a pattern, with an input of at least one of the frame signal data of each of the sub regions or a feature quantity extracted from the frame signal data Therefore, image processing can be applied with a more suitable parameter for each site.

The identifier R22 classifies frame signal data of each of the sub regions in accordance with a pattern, with an input of patient information of the subject and an input of at least one of the frame signal data of each of the sub regions or a feature quantity extracted from the frame signal data. Therefore, image processing can be applied with a more suitable parameter for each site of the subject in patient information.

Further, the identifier R22 classifies frame signal data of each of the sub regions in accordance with a pattern, with an input of diagnostic use information and an input of at least one of the frame signal data of each of the sub regions or a feature quantity extracted from the frame signal data. Therefore, image processing can be applied with a more suitable parameter for each site corresponding to the diagnostic use information.

The transmission part 3 generates a B mode drive signal and inputs the generated B mode drive signal to the ultrasonic probe 101. The reception part 4 generates a reception signal of a B mode from an electric signal generated by the ultrasonic probe 101. The frequency filter part 51, the envelope detection part 52, and the logarithm compression part 53 generate B mode frame signal data from the reception signal. The identifier R22 classifies frame signal data of each of the sub regions in accordance with a structure of a speckle pattern. Therefore, image processing can be applied with a suitable parameter for each site for the B mode image.

The pattern classification part R2 includes the feature quantity extraction part R21 that extracts a feature vector as at least one feature quantity of presence/absence, density; a particle size, and contrast of the speckle pattern, from the frame signal data of each of the sub regions. The identifier R22 classifies frame signal data of each of the sub regions, with an input of a feature vector. Therefore, image processing can be applied with a more suitable parameter for each site for the B mode image.

The identifier R22 is a convolutional neural network and has a convolutional filter that performs convolutional filtering, with an input of frame signal data of each of the sub regions. Therefore, a burden of extracting the feature quantity can be reduced, and image processing can be applied with a more suitable parameter for each site for the B mode image.

The image processing execution part R5 executes image processing including at least one of smoothing, edge emphasis, persistence, or gradation conversion. Therefore, an appropriate type of image processing can be applied with a suitable parameter for each site for the B mode image.

The transmission part 3 generates a C mode drive signal, and inputs the generated C mode drive signal to the ultrasonic probe 101. The reception part 4 generates a reception signal of a C mode from an electric signal generated by the ultrasonic probe 101. The quadrature detection circuit 71, the corner turn control part 72, the MTI filter 73, the correlation operation part 74, and the data conversion part 75 generate C mode frame signal data from the reception signal. The identifier R22 classifies frame signal data of each of the sub regions in accordance with at least one pattern of a blood flow or noise. Therefore, image processing can be applied with a suitable parameter for each site for the C mode image.

The pattern classification part R2 includes the feature quantity extraction part R21 that extracts a feature vector as at least one feature quantity of a thickness and a direction of the blood flow; and presence/absence, density, and a particle size of noise, from the frame signal data of each of the sub regions for one frame. The identifier R22 classifies frame signal data of each of the sub regions, with an input of a feature vector. Therefore, image processing can be applied with a more suitable parameter for each site from a still image for the C mode image.

Further, the pattern classification part R2 includes the feature quantity extraction part R21 that extracts a feature vector as at least one feature quantity of: a thickness, a direction, and pulsatility of the blood flow; and presence/ absence, density, a particle size, and interframe variation of noise, from the frame data of each of the sub regions for consecutive plural frames. The identifier R22 classifies frame signal data of each of the sub regions, with an input of a feature vector. Therefore, image processing can be applied with a more suitable parameter for each site from a dynamic image for the C mode image.

The identifier R22 is a convolutional neural network and has a convolutional filter that performs convolutional filtering, with an input of frame signal data of each of the sub regions for one frame or consecutive plural frames. Therefore, a burden of extracting the feature quantity can be reduced, and image processing can be applied with a more suitable parameter for each site for the C mode image.

Further, the image processing execution part R5 executes image processing including at least one of smoothing, edge emphasis, persistence, or a noise cut process. Therefore, an appropriate type of image processing can be applied with a suitable parameter for each site for the C mode image.

The ultrasonic diagnostic apparatus 100 further includes the operation part 2 that receives an input of a type of a parameter for image processing. The parameter selection part R4 selects a parameter in accordance with the inputted type of a parameter and a classification result of each of the sub regions. Therefore, image processing can be automatically applied with a suitable type of a parameter for each site based on the appropriate type selected by the user and the classification result.

Further, the parameter selection part R4 selects a parameter of a preset type in accordance with the classification result of each of the sub regions. Therefore, image processing can be automatically applied with a suitable type of a parameter for each site while the operation burden of the user can be reduced.

The ultrasonic diagnostic apparatus 100 further includes the control part 9 that stores, in the storage part 11, the frame signal data before image processing stored in the frame data storage part 10 and corresponding to the ultrasonic image data subjected to image processing. Therefore, by storing and using the frame signal data before image processing as mechanical learning data for the identifier R22, a more appropriate identifier R22 can be constructed.

Further, in accordance with an instruction for storage of composite image data as ultrasonic image data subjected to image processing, the control part 9 stores, in the storage part 11, composite image data subjected to the instructed image processing and frame signal data before image processing corresponding to the ultrasonic image data subjected to image processing. Therefore, by storing and using the frame signal data before image processing associated with the composite image data as mechanical learning data for the identifier R22, a more appropriate identifier R22 can be constructed.

Further, the control part 9 stores, in the storage part 11: composite image data subjected to the instructed image processing; frame signal data before image processing corresponding to composite image data subjected to image processing; at least one of text annotation information, body mark information, or diagnostic use information that are attached to composite image data subjected to image processing. Therefore, by storing and using, as mechanical learning data for the identifier R22, frame signal data before image processing associated with the composite image data, at least one of text annotation information, body mark information, or diagnostic use information, a more appropriate identifier R22 can, be constructed.

Modification

Figure 6A:
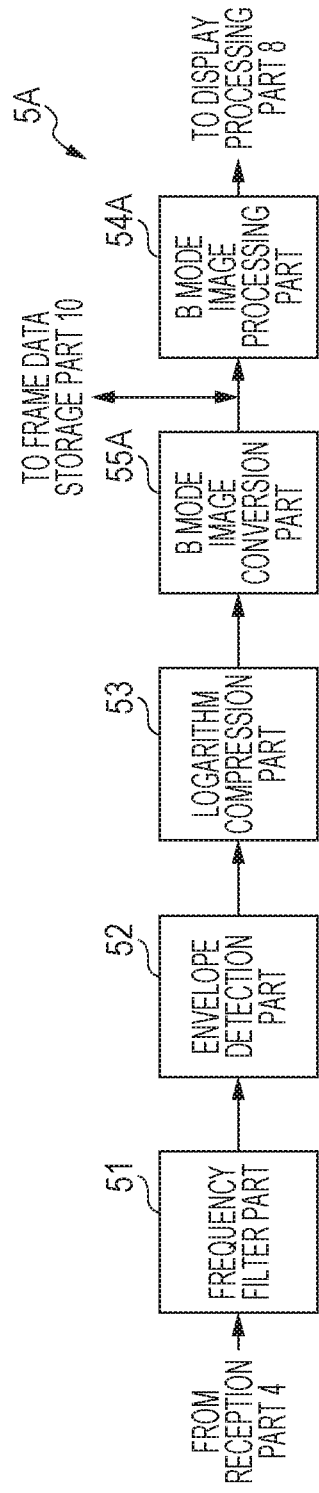
FIG. 6A is a schematic block diagram showing an internal configuration of a B mode image generation part according to a modification.
Figure 6B:
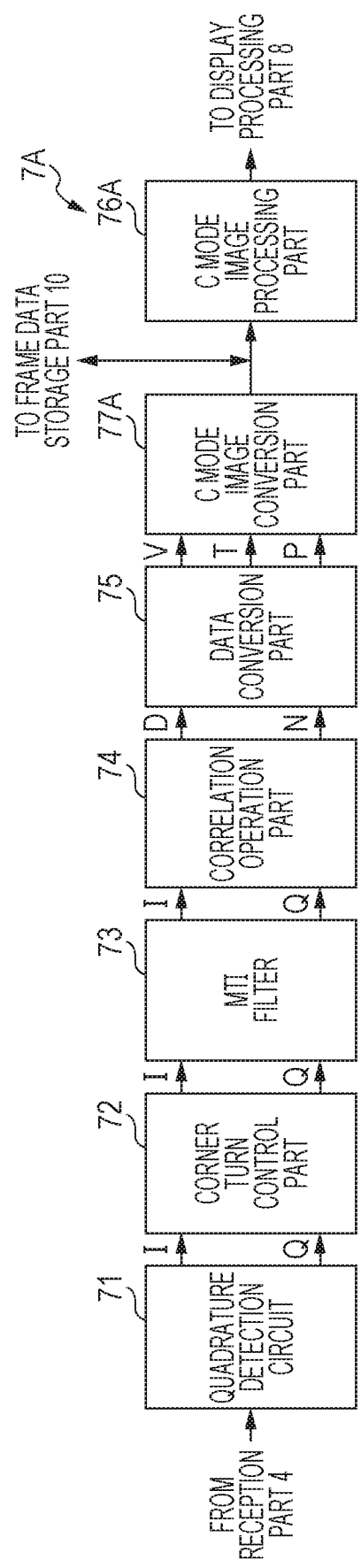
FIG. 6B is a schematic block diagram showing an internal configuration of a C mode image generation part according to the modification.

A modification of the above embodiment will be described with reference to FIGS. 6A and 6B. However, the same reference numerals are given to the same constituent parts as those in the above embodiment, and the description thereof will be omitted. FIG. 6A is a schematic block diagram showing an internal configuration of a B mode image generation part 5A according to the modification. FIG. 6B is a schematic block diagram showing an internal configuration of a C mode image generation part 7A according to the modification.

In a configuration of an ultrasonic diagnostic apparatus 100 of the present modification, the B mode image generation part 5 and the C mode image generation part 7 of the above embodiment are replaced with the B mode image generation part 5A shown in FIG. 6A and the C mode image generation part 7A shown in FIG. 6B.

As shown in FIG. 6A, the B mode image generation part 5A includes a frequency fiber part 51, an envelope detection part 52, a logarithm compression part 53, a B mode image conversion part 55A, and a B mode image processing part 54A.

Similarly to the B mode image conversion part 55, under control of a control part 9, the B mode image conversion part 55A generates B mode image data as frame data and outputs to a frame data storage part 10, by performing coordinate conversion as a DSC on B mode frame signal data subjected to logarithm compression and inputted from the logarithm compression part 53, and performing grayscale mapping. The frame data storage part 10 stores the B mode image data inputted from the B mode image conversion part 55A.

The B mode image processing part 54A has the same configuration as the B mode image processing part 54, reads B mode image data for one frame stored in the frame data storage part 10 under control of the control part 9, and executes image processing on the read B mode image data for one frame.

As shown in FIG. 6B, the C mode image generation part 7A includes a quadrature detection circuit 71, a corner turn control part 72, an MTI filter 73, a correlation operation part 74, a data conversion part 75, a C mode image conversion part 77A, and a C mode image processing part 76A.

Similarly to the C mode image conversion part 77, under control of the control part 9, the C mode image conversion part 77A generates C mode image data of an ROI as frame data in a specification mode specified by the user of C mode and outputs to the frame data storage part 10, by performing coordinate conversion as the a DSC on the frame signal data subjected to the data conversion and inputted from the data conversion part 75, and performing color mapping. The frame data storage part 10 stores the C mode image data inputted from the C mode image conversion part 77A.

Similarly to the C mode image processing part 76, under control of the control part 9, the C mode image processing part 76A reads C mode image data for one frame or latest consecutive plural frames stored in the frame data storage part 10, and executes image processing on the C mode image data for one frame with use of the read C mode image data for one or plural frames.

As described above, according to this modification, the same effects as those of the above-described embodiment can be obtained. In particular, in a case where the identifier R22 is a convolutional neural network, the identifier R22 has a convolution filter that performs convolutional filtering, with an input of B mode image data and C mode image data of each of the sub regions for one frame or consecutive plural frames. Therefore, a burden of extracting the feature quantity can be reduced, and image processing can be applied with a more suitable parameter for each site for the B mode image and the C mode image.

It is to be noted that the descriptions in the above embodiment and modification are examples of a suitable medical image processing apparatus according to the present invention, and the present invention is not limited to these.

For example, the configuration of the image processing part in the above embodiment and modification (the region dividing part R1, the pattern classification part R2, the parameter holding part R3, the parameter selection part R4, and the image processing execution part R5) may be a configuration that is applied to a medical image processing apparatus for other than an ultrasonic image. For example, it is also possible to adopt a medical image processing apparatus that scans the subject to generate frame data (frame signal data or frame image data), executes image processing similar to that of the image processing part according to the above embodiment and modification on the frame data, and generates medical image data. This medical image processing apparatus is, for example, an X-ray imaging apparatus (computed radiography (CR) apparatus), a computed tomography (CT) apparatus, a nuclear magnetic resonance (MRI) device, or the like, while the medical image data is X-ray image data, CT image data, MRI image data, or the like.

Further, appropriate changes may be made within the range not departing from the gist of the present invention, for the detailed structure and detailed operation of each part constituting the ultrasonic diagnostic apparatus 100 in the above embodiment.

Although embodiments of the present invention have been described and illustrated in detail, the disclosed embodiments are made for purposes of illustration and example only and not limitation. The scope of the present invention should be interpreted by terms of the appended claims.

What is claimed is:

1. A medical image processing apparatus comprising:
    a frame data generation part that generates frame data by scanning a subject;
    an image generation part that applies image processing on the generated frame data to generate medical image data;
    an ultrasonic probe that transmits a transmission ultrasonic wave to the subject according to a drive signal and receives a reflected ultrasonic wave;
    a transmission part that generates the drive signal and outputs the generated drive signal to the ultrasonic probe; and
    a reception part that generates a reception signal from an electric signal generated by the ultrasonic probe;
    wherein:
    the image generation part comprises:
        a region dividing part that divides the generated frame data into a plurality of sub regions by applying a grid on the frame;
        a pattern classification part including an identifier that classifies frame data of each of the sub regions according to a pattern;
        a parameter selection part that selects a parameter for image processing for each sub region based on a classification result of each of the sub regions; and
        an image processing execution part that applies image processing on the frame data of each of the sub regions with use of a selected parameter of each of the sub regions,
    the frame data generation part generates frame data from the reception signal,
    the pattern classification part classifies the frame data of each of the sub regions based on a type of organ of the subject,
    the drive signal is a B mode drive signal,
    the reception signal generated by the reception part is a B mode signal,
    the frame data generation part generates B mode frame data from the reception signal,
    the identifier classifies the frame data of each of the sub regions based on a structure of a speckle pattern, and
    the image processing execution part executes image processing including at least one of smoothing, edge enhancement, persistence, and gradation conversion.

2. The medical image processing apparatus according to claim 1, wherein, the identifier is based on machine learning and classifies the frame data of each of the sub regions based on an input of at least one of the frame data of each of the sub regions and a feature quantity extracted from the frame data.

3. The medical image processing apparatus according to claim 2, wherein, the identifier classifies the frame data of each of the sub regions based on an input of patient information of the subject and an input of at least one of the frame data of each of the sub regions and a feature quantity extracted from the frame data.

4. The medical image processing apparatus according to claim 2, wherein, the identifier classifies the frame data of each of the sub regions based on an input of diagnostic use information and an input of at least one of the frame data of each of the sub regions and a feature quantity extracted from the frame data.

5. The medical image processing apparatus according to claim 2, wherein:
    the transmission part further generates a C mode drive signal, and inputs the generated C mode drive signal to the ultrasonic probe,
    the reception part further generates a reception signal of a C mode from an electric signal generated by the ultrasonic probe,
    the frame data generation part further generates C mode frame data from the reception signal, and
    the identifier classifies the frame data of each of the sub regions based on at least one pattern of a blood flow and noise.

6. The medical image processing apparatus according to claim 5, wherein:
    the pattern classification part includes a feature quantity extraction part that extracts a feature vector as at least one feature quantity of: a thickness and a direction of a blood flow; and presence/absence, density, and a particle size of noise, from the frame data of each of the sub regions for one frame, and the identifier classifies the frame data of each of the sub regions, based on an input of the feature vector.

7. The medical image processing apparatus according to claim 5, wherein:
the pattern classification part includes a feature quantity extraction part that extracts a feature vector as at least one feature quantity of: a thickness, a direction, and pulsatility of a blood flow; and presence/absence, density, a particle size, and interframe variation of noise, from the frame data of each of the sub regions for consecutive plural frames, and
the identifier classifies the frame data of each of the sub regions, based on an input of the feature vector.

8. The medical image processing apparatus according to claim 5, wherein the identifier is a convolutional neural network, and has a convolutional filter that performs convolutional filtering, with an input of the frame data of each of the sub regions for one frame or consecutive plural frames.

9. The medical image processing apparatus according to claim 5, wherein the image processing executed by the image processing execution part further includes noise cut.

10. The medical image processing apparatus according to claim 1, wherein:
the pattern classification part includes a feature quantity extraction part that extracts a feature vector as at least one feature quantity of: presence/absence, density, a particle size, and contrast of a speckle pattern from the frame data of each of the sub regions, and
the identifier classifies the frame data of each of the sub regions, based on an input of the feature vector.

11. The medical image processing apparatus according to claim 1, wherein the identifier is a convolutional neural network, and has a convolutional filter that performs convolutional filtering, with an input of the frame data of each of the sub regions.

12. The medical image processing apparatus according to claim 1, further comprising an operation part that inputs a type of parameter for the image processing, wherein
the parameter selection part selects a parameter of the inputted type according to the inputted type of parameter and a classification result of each of the sub regions.

13. The medical image processing apparatus according to claim 1, wherein the parameter selection part selects a parameter of a preset type according to a classification result of each of the sub regions.

14. The medical image processing apparatus according to claim 1, further comprising a hardware processor that stores the frame data before the image processing corresponding to ultrasonic image data subjected to the image processing in a storage destination.

15. The medical image processing apparatus according to claim 14, wherein, in response to an instruction for storage of ultrasonic image data as medical image data subjected to image processing, the hardware processor stores:
ultrasonic image data subjected to image processing of the instruction for storage; and
the frame data before image processing corresponding to ultrasonic image data subjected to the image processing in the storage destination.

16. The medical image processing apparatus according to claim 15, wherein, the hardware processor stores: ultrasonic image data subjected to image processing of the instruction for storage; the frame data before image processing corresponding to ultrasonic image data subjected to the image processing; and at least one of text annotation information, body mark information, and diagnostic use information that are attached to ultrasonic image data subjected to the image processing, in the storage destination.

17. A medical image processing method comprising:
generating frame data by scanning a subject; and
applying image processing on the generated frame data and generating medical image data,
transmitting, by a ultrasonic probe, a transmission ultrasonic wave to the subject according to a drive signal and receiving a reflected ultrasonic wave;
generating the drive signal and outputting the generated drive signal to the ultrasonic probe; and
generating a reception signal from an electric signal generated by the ultrasonic probe;
wherein:
the image processing includes:
dividing the generated frame data into frame data of a plurality of sub regions by applying a grid on the frame;
classifying frame data of each of the sub regions according to a pattern;
selecting a parameter for image processing for each sub region based on a classification result of each of the sub regions; and
applying image processing on the frame data of each of the sub regions with use of a selected parameter of each of the sub regions,
the frame data is generated from the reception signal,
the classifying of the frame data of each of the sub regions is based on a type of organ of the subject,
the drive signal is a B mode drive signal,
the reception signal is a B mode signal,
the frame data is B mode frame data generated from the reception signal,
the classifying of the frame data of each of the sub regions is based on a structure of a speckle pattern, and
the image processing further includes at least one of smoothing, edge enhancement, persistence, and gradation conversion.

18. A non-transitory recording medium storing a computer readable medical image processing program causing a computer to perform:
generating frame data by scanning a subject; and
applying image processing on the generated frame data and generating medical image data,
transmitting, by a ultrasonic probe, a transmission ultrasonic wave to the subject according to a drive signal and receiving a reflected ultrasonic wave;
generating the drive signal and outputting the generated drive signal to the ultrasonic probe; and
generating a reception signal from an electric signal generated by the ultrasonic probe;
wherein:
the image processing includes:
dividing the generated frame data into frame data of a plurality of sub regions by applying a grid on the frame;
classifying frame data of each of the sub regions according to a pattern;
selecting a parameter for image processing for each sub region based on a classification result of each of the sub regions; and
applying image processing on the frame data of each of the sub regions with use of a selected parameter of each of the sub regions,
the frame data is generated from the reception signal, the classifying of the frame data of each of the sub regions is based on a type of organ of the subject,
the drive signal is a B mode drive signal,
the reception signal is a B mode signal,
the frame data is B mode frame data generated from the reception signal,
the classifying of the frame data of each of the sub regions is based on a structure of a speckle pattern, and
the image processing further includes at least one of smoothing, edge enhancement, persistence, and gradation conversion.

* * * * *